United States Patent [19]

Noda et al.

[11] Patent Number: 5,380,899
[45] Date of Patent: Jan. 10, 1995

[54] PROCESS FOR THE PRODUCTION OF CYCLIC AMIDINE

[75] Inventors: Seiji Noda, Chiba; Takeshi Tsuji, Narashino, both of Japan

[73] Assignee: Lion Akzo Co., Ltd., Japan

[21] Appl. No.: 183,888

[22] Filed: Jan. 21, 1994

[30] Foreign Application Priority Data

Apr. 22, 1993 [JP] Japan ................................. 5-118954

[51] Int. Cl.$^6$ ................................. C07F 7/10
[52] U.S. Cl. ................................. 556/407; 544/242; 544/336; 548/347.1
[58] Field of Search ................................. 544/242, 336; 548/347.1; 556/407

[56] References Cited

U.S. PATENT DOCUMENTS 4,031,015  6/1977  Miller ............................ 556/407 UX
5,171,764 12/1992  Katayama et al. .......... 556/407 UX

*Primary Examiner*—Paul F. Shaver
*Attorney, Agent, or Firm*—Lorusso & Loud

[57] ABSTRACT

A cyclic amidine typically having the formula:

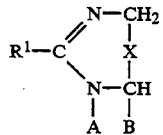

wherein $R^1$ represents an organic radical, X represents a direct bond or a divalent organic radical and A and B each represent hydrogen or an organic radical is prepared by a liquid phase reaction of a nitrile of the formula $R^1CN$ where $R^1$ has the same meaning as above, with a polyamine typically having the formula:

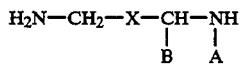

where X, A and B have the same meaning as above, in the presence presence of a mixture of a titanium compound with water.

14 Claims, No Drawings

PROCESS FOR THE PRODUCTION OF CYCLIC AMIDINE

BACKGROUND OF THE INVENTION

This invention relates to a process for the production of a cyclic amidine.

A number of processes have thus far been proposed for the production of a cyclic amidine such as a 2-imidazoline compound. For example, JP-B-39-24965 discloses a process in which a nitrile is reacted with a diamine in the presence of sulfur for the production of a 2-imidazoline compound. This process has a problem because the process requires the removal of harmful hydrogen sulfide. JP-A-55-83753 suggests a vapor phase reaction, of a nitrile with a diamine. This process has a problem that specifically limited conditions and apparatuses are required and the yield of the amidine product is low. JP-A-59-84873 discloses a process in which a nitrile is reacted with a diamine in the presence of copper acetate monohydrate. This process has a problem because by-products are formed in a large amount. JP-A-3-163064 proposes the reaction of a nitrile or a carboxylic acid with a diamine in the presence of gamma-alumina or silica. This process requires a reaction temperature of as high as 300° C. so that a specific reactor is required. Further, a large amount of by-products is unavoidably yielded. DE-A-2154948 discloses the reaction of oxazoline with ethylene diamine or 1,3-propanediamine for the production of an imidazoline or pyrimidin compound. The use of oxazoline as a raw material is, however, disadvantageous from the standpoint of economy. This process also has a problem because the yield is low.

SUMMARY OF THE INVENTION

It is, therefore, the prime object of the present invention to provide an economical process which can produce a cyclic amidine with a high yield.

Another object of the present invention is to provide a process for the production of a cyclic amidine, such as a 2-imidazoline derivative or a pyrimidin derivative, which permits the use of a relatively low reaction temperature of not higher than 250° C. and which does not require a specific, complicated reactor.

It is a further object of the present invention to provide a process of the above-mentioned type which can produce high grade amidines having a good hue and free of odors attributed to impurities.

In accordance with one aspect of the present invention there is provided a process for the production of a cyclic amidine, wherein a nitrile is reacted with a polyamine in a liquid phase, said process being characterized in that the reaction is performed in the presence of a mixture of water with a titanium compound as a catalyst.

In another aspect, the present invention provides a process for the production of a cyclic amidine expressed by the following general formula (I):

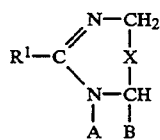 (I)

wherein $R^1$ stands for an aliphatic group, an alicyclic group, an aromatic group or a heterocyclic group, X stands for a direct bond or a divalent organic radical and A and B stand, independently from each other, for hydrogen or an organic group, comprising a step of reacting a nitrile having the following general formula (II):

$$R^1CN \qquad (II)$$

wherein $R^1$ has the same meaning as above, with a polyamine having the following general formula (III):

 (III)

wherein X, A and B have the same meaning as above, at a temperature of 130°–250° C. in the presence of a mixture of water with a catalytically effective amount of a titanium compound.

Other objects, features and advantages of the present invention will become apparent from the detailed description of the preferred embodiment to follow.

DETAILED DESCRIPTION OF THE PREFERRED EMBODIMENTS OF THE INVENTION

In the present invention, a nitrile is reacted with a polyamine in a liquid phase in the presence of a mixture of water with a titanium compound to produce an amidine compound.

The nitrile is preferably a compound having the following general formula (II):

$$R^1CN \qquad (II)$$

wherein $R^1$ stands for an aliphatic group, such as an alkyl group or alkenyl group having 1–30 carbon atoms, an alicyclic group, such as a cycloalkyl group, e.g. cyclohexyl, an aromatic group, such as aryl or aralkyl, or a heterocyclic group. A homopolymer or copolymer of acrylonitrile may also be used as the nitrile. The aliphatic group may contain one or more heteroatoms, such as oxygen, nitrogen and sulfur, in the skeletal chain thereof. Illustrative of suitable nitriles are acetonitrile, propionitrile, benzonitrile, 1,3-dicyanobenzene, 1,4-dicyanobenzene, adiponitrile, lauronitrile, myristonitrile, palmitonitrile, stearonitrile, oleonitrile, caprylonitrile, caprylonitrile, arachidonitrile, behenonitrile and copolymers of acrylonitrile and methylacrylate.

The polyamine is preferably a compound having the following general formula (III):

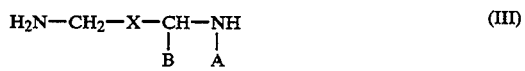 (III)

wherein X stands for a direct bond or a divalent organic radical and A and B stand, independently from each other, for hydrogen or an organic group.

The divalent organic radical X may be, for example, an aliphatic group, alicyclic group, an aromatic group or a heterocyclic group and can have a terminal end atom of carbon, nitrogen, oxygen, sulfur or the like heteroatom. The aliphatic group may contain one or more heteroatoms, such as oxygen, nitrogen and sulfur, in the skeletal chain thereof.

The organic group for the symbols A and B of the formula (III) may be, for example, alkyl, cycloalkyl, aryl or aralkyl and can have a terminal end atom of carbon, nitrogen, oxygen, sulfur or the like heteroatom. When the organic group is an aliphatic group, one or more heteroatoms, such as oxygen, nitrogen and sulfur, may be present in the skeletal chain thereof.

When X of the formula (III) is a direct bond, namely when the polyamine is a 1,2-diamino compound, the cyclic amidine produced is a 2-imidazoline compound. Such a polyamine may be a compound expressed by the following formula (IV) or (V):

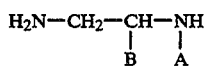   (IV)

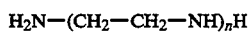   (V)

wherein A and B have the same meaning as above and n is an integer of 2-5. Illustrative of suitable compounds of the formula (IV) are 1,2-diaminoethane, 1,2-diaminopropane, 1,2-diamino-n-butane, 1,2-diamino-n-pentane, 1,2-diamino-n-hexane, 1,2-diamino-n-heptane, 1,2-diamino-n-octane, 1,2-diamino-n-nonane, N-benzylethylene-diamine, N-phenylethyelenediamine, N-methylethyelenediamine, N-ethylethylenediamine, 2-(2-aminoethylamino)ethanol, N-($\beta$-aminoethyl)-$\gamma$-aminopropyl(dimethoxy)methylsilane, and N-($\beta$-aminoethyl)-$\gamma$-aminopropyltrimethoxysilane. Examples of the compounds of the formula (V) include diethylenetriamine, triethylenetetramine, tetraethylene-pentamine and pentaethylenehexamine.

The divalent organic radical for the symbol X of the formula (III) may be, for example, alkylene, cycloalkylene, arylene, an aromatic radical having the formula —R$^2$—Ar—R$^2$— where R$^2$ and R$^3$ stand independently from each other for alkylene and Ar stands for arylene, and a radical having the formula

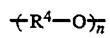

where R$^4$ stands for an alkylene and n is an integer of 1-5.

Preferably, the polyamine of the formula (III) in which X represents a divalent organic radical is expressed by the formula (VI):

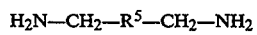   (VI)

wherein R$^5$ is an alkylene having 1-22 carbon atoms, more preferably 1-18 carbon atoms. Examples of suitable polyamine of the formula (VI) include 1,3-diaminopropane, 1,4-diaminobutane, 1,5-diaminopentane, 2,2-dimethylpropylene diamine, 1,6-diaminohexane, 1,7-diaminopentane, 1,8-diaminooctane, 1,9-diaminononane and 1,12-diaminododecane.

Examples of polyamines which are not represented by the formula (III) include 3-(2-aminoethyl)indole and 4-aminodiphenylamine.

By the reaction of the nitrile of the formula (II) with the polyamine of the formula (III), a cyclic amidine expressed by the following general formula (I) may be obtained:

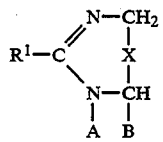   (I)

wherein R$^1$, X, A and B are as defined above.

The titanium compound to be used as a catalyst in the present invention may be an organic titanium compound, a titanium halide or titanium hydroxide and is preferably a tetravalent titanium compound. Both liquid and solid catalyst may be used. The use of a titanium compound capable of reacting with water to produce an oligomer (preferably dimer) of the titanium compound is preferred.

The organic titanium compound is preferably a compound having the formula:

Ti(OR$^6$)$_4$,
Ti(OR$^6$)$_3$(OCOR$^7$),
(HOR$^8$O)$_2$Ti(OR$^6$)$_2$ or
(H$_2$NR$^8$O)$_2$Ti(OR$^6$)$_2$ wherein R$^6$ and R$^7$ stand, independently from each other, for a hydrocarbyl group having 1-20 carbons, such as alkyl, cycloalkyl, aryl or aralkyl, and R$^8$ stands for an aliphatic or aromatic divalent radical having 1-20 carbons.

Examples of suitable titanium compounds are titanium tetraisopropoxide, titanium tetra-n-butoxide, titanium tetrakis-2-ethyleneoxide, titanium tetrastearoxide, di-isopropoxybis(acetylacetonate)titanium, isopropoxy(2-ethyl-1,3-hexanedioleato)titanium of the formula Ti(O—iC$_3$H$_7$)$_n$· [OCH$_2$CH(C$_2$H$_5$)CHOHC$_3$H$_7$]$_{4-n}$, di-n-butoxybis(triethanolaminato)titanium, dihydroxybis(lactato)titanium, titanium tetrachloride, titanium tetrabromide, titanium tetrafluoride, titanium tetraiodide and titanium tetrahydroxide.

The reaction of the nitrile with the polyamine is preferably performed at a temperature of 130°-250° C., preferably 180°-220° C., in the presence of a mixture of water with a catalytically effective amount of the titanium compound. When the reaction temperature is lower than 130° C., the reaction rate is considerably small, on the other hand, too high a reaction temperature in excess of 250° C. causes side reactions and results in the deterioration of the quality of the amidine product. The reaction pressure is generally 0-100 kg/cm$^2$ G, preferably 0-10 kg/cm$^2$ G. The reaction time depends upon the reaction temperature and pressure and the amount of the catalyst but is generally 2-24 hours.

The amount of the catalyst is generally 0.1-5% by weight, preferably 0.5-3% by weight, based on the nitrile used. The catalyst may be used in an amount of more than 5% but no additional merit is obtainable. Too low an amount of the catalyst below 0.1 requires an increased reaction time. Water is generally used in an amount of 1-300% by weight, preferably 10-80% by weight, based on the titanium compound. Too low an amount of water requires an increased reaction time. When the amount of water exceeds 300% by weight, the amidine-forming reaction fails to effectively proceed.

In one preferred embodiment, the reaction of the nitrile with the polyamine is carried out in the following manner. A titanium compound is reacted with water, generally at a temperature of 0°-150° C., to hydrolyze the titanium compound with the simultaneous polymerization thereof, so that a first mixture containing an oligomer (preferably a dimer) of the titanium compound having a Ti—O—Ti unit is obtained. The first mixture is preferably treated for removing distillable components such as unreacted water and a by-product, such as an alcohol, formed in situ by the hydrolysis of the titanium compound, thereby to obtain a second mixture containing the oligomer. The nitrile is reacted with the polyamine in the presence of the first or the second mixture.

The reaction product is purified in any known manner such as by recrystallization or distillation. The amidine product is utilized for a wide variety of applications especially as raw materials for epoxy resin curing agents, medicines, photo or heat sensitive materials, preservatives, water-treating agents, etc.

The following examples will further illustrate the present invention.

EXAMPLE 1

In a 500 ml SUS 316L stainless steel autoclave were charged 120 g of ethylene diamine, 82 g of acetonitrile and 2 g of titanium tetraisopropoxide. After addition of 1 g of water, the mixture was heated up to 200° C. with stirring. As the reaction proceeded, the pressure within the autoclave was found to increase to 45 kg/cm$^2$G at maximum due to the formation of ammonia. After 3 hours from the commencement of the reaction, the ammonia was discharged overhead from the autoclave. The reaction mixture was then dissolved in 250 ml of acetone and crystallized to obtain 126 g of 2-methyl-2-imidazoline having a melting point of 102.5°–103.2° C. with a yield of 75%. Gas chromatographic analysis reveals that this product has a purity of 99%.

EXAMPLE 2

In a 500 ml SUS 316L stainless steel autoclave were charged 148 g of 1,2-diaminopropane, 110 g of propionitrile and 3 g of titanium tetrachloride. After addition of 2 g of water, the mixture was heated up to 200° C. with stirring. As the reaction proceeded, the pressure within the autoclave was found to increase to 50 kg/cm$^2$G at maximum due to the formation of ammonia. After 3 hours from the commencement of the reaction, the ammonia was discharged overhead from the autoclave. The reaction mixture was then subjected to vacuum distillation at 0.5 mmHg and at 98°–110° C. to obtain 191 g of 2-ethyl-4-methyl-2-imidazoline with a yield of 85%.

EXAMPLE 3

In a 2,000 ml four-necked flask equipped with a reflux condenser and a thermometer were charged 515 g of benzonitrile and 10 g of titanium diisopropoxybis(acetonate). After addition of 4 g of water, the mixture was heated up to 185°–190° C. with stirring. Then, 300 g of ethylenediamine were added dropwise for 10 hours with stirring while maintaining the temperature at 185° C. or above. After completion of the addition of the diamine, the reaction mixture was heated up to 200° C. and maintained at that temperature for 6 hours. The resulting mixture was then subjected to vacuum distillation at 0.7 mmHg and at 160°–180° C. to obtain 635 g of 2-phenyl-2-imidazoline with a yield of 87%.

EXAMPLE 4

In a 500 ml four-necked flask equipped with a reflux condenser and a thermometer were charged 181 g of lauronitrile and 2 g of titanium tetraisopropoxide. Further, 1 g of water was added with stirring and the mixture was heated up to about 120° C. with stirring for 10 minutes. Thereafter, while maintaining the temperature at about 120° C., the mixture was heated for 30 minutes under a reduced pressure to remove isopropanol formed in situ and unreacted water therefrom. After heating the mixture up to 200°–210° C., 74 g of 1,2-diaminopropane were added dropwise for 120 hours with stirring while maintaining the temperature at 200° C. or above. After the addition of the diaminopropane had been completed, the reaction mixture was heated at 210°–220° C. for 4 hours for the completion of the reaction. The resulting mixture was then subjected to vacuum distillation at 1.0 mmHg and at 160°–165° C. to obtain 219 g of 2-undecyl-4-methyl-2-imidazoline with a yield of 92%.

EXAMPLE 5

In a 500 ml SUS 316L stainless steel autoclave were charged 60 g of ethylene diamine, 267 g of stearonitrile and 2.5 g of titanium tetraisopropoxide. After addition of 1 g of water, the mixture was heated up to 210° C. with stirring and maintained at that temperature for 4 hours while removing ammonia produced in situ to maintain the pressure within the autoclave at 8–9 kg/cm$^2$G. The resulting mixture was then subjected to vacuum distillation at 0.6 mmHg and at 230°–235° C. to obtain 267 g of 2-heptadecyl-2-imidazoline with a yield of 86%.

Comparative Example 1

Example 1 was repeated in the same manner as described except that no water was added. The yield of 2-methyl-2-imidazoline was only 6%.

Comparative Example 2

Example 4 was repeated in the same manner as described except that no water was added. It was necessary to add 1,2-diaminopropane very slowly in order to maintain the reaction temperature at above 200° C. under suitable refluxing conditions. Thus, the amount of 1,2-diaminopropane added to the flask was only 7 g after 12 hours from the commencement of the addition. The yield of 2-undecyl-4-methyl-2-imidazoline was only 5%.

EXAMPLE 6

In a 500 ml SUS 316L stainless steel autoclave were charged 148.3 g (2 moles) of 1,3-diaminopropane, 82.1 g (2 moles) of acetonitrile and 2 g of titanium tetraisopropoxide. After addition of 1 g of water, the mixture was heated up to 200° C. with stirring. As the reaction proceeded, the pressure within the autoclave was found to increase to 45 kg/cm$^2$G at maximum due to the formation of ammonia. After 3 hours from the commencement of the reaction, the ammonia was discharged overhead from the autoclave. The reaction mixture was filtered to remove the catalyst. The NMR analysis of the product revealed that 2-methylpyrimidine was prepared with a purity of 98% or more.

EXAMPLE 7

In a 500 ml SUS 316L stainless steel autoclave were charged 176.3 g (2 moles) of 1,4-diaminobutane, 110 g (2 moles) of propionitrile and 3 g of titanium tetrachloride. After addition of 2 g of water, the mixture was heated up to 200° C. with stirring. As the reaction proceeded, the pressure within the autoclave was found to increase to 50 kg/cm$^2$G at maximum due to the formation of ammonia. After 3 hours from the commencement of the reaction, the ammonia was discharged overhead from the autoclave. The reaction mixture was filtered to remove the catalyst. The NMR analysis of the product revealed that a cyclic 2-ethylamidine compound (a compound of the formula (I) in which $R^1$ is $-C_2H_5$, X is $-(CH_2)_2-$, A is H and B is H) was prepared with a purity of 92% or more.

EXAMPLE 8

In a 2,000 ml four-necked flask equipped with a reflux condenser and a thermometer were charged 515 g (5 moles) of benzonitrile and 10 g of titanium diisopropoxybis(acetonate). After addition of 4 g of water, the mixture was heated up to 185°–190° C. with stirring. Then, 370.7 g (5 moles) of 1,3-diaminopropane were added dropwise for 4 hours with stirring while maintaining the temperature at 185° C. or above. After completion of the addition of the diamine, the reaction mixture was heated up to 220° C. for and maintained at that temperature for 2 hours for completion of the reaction. The NMR analysis of the product revealed that 2-phenylpyrimidine was prepared with a purity of 98% or more.

EXAMPLE 9

In a 1,000 ml four-necked flask equipped with a reflux condenser and a thermometer were charged 181 g (1 mole) of lauronitrile and 2 g of titanium tetraisopropoxide. After addition of 1 g of water, the mixture was heated up to 200° C. with stirring. Then, 102 g (1 mole) of 1,5-diaminopentane were added dropwise for 4 hours with stirring while maintaining the temperature at 200° C. or above. After completion of the addition of the 1,5-diaminopentane, the reaction mixture was heated for 2 hours for completion of the reaction. The NMR analysis of the product revealed that a cyclic 2-undecylamidine compound (a compound of the above formula (I) in which $R^1$ is $-C_{11}H_{23}$, X is $-(CH_2)_3-$, A is H and B is H) was prepared with a purity of 96%.

EXAMPLE 10

In a 1,000 ml four-necked flask equipped with a reflux condenser and a thermometer were charged 265 g (1 mole) of stearonitrile at 50° C. and 3 g of titanium tetraisopropoxide. After addition of 1.5 g of water, the mixture was heated up to 200° C. with stirring. Then, 74.1 g (1 mole) of 1,3-diaminopropane were added dropwise for 4 hours with stirring while maintaining the temperature at 200° C. or above. After completion of the addition of the 1,3-diaminopropane, the reaction mixture was heated for 2 hours for completion of the reaction. The NMR analysis of the product revealed that 2-heptadecylpyrimidine was prepared with a purity of 98% or more.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A process for the production of a cyclic amidine, wherein a nitrile is reacted with a polyamine in a liquid phase, said process being characterized in that the reaction is performed in the presence of a mixture of water with a titanium compound as a catalyst.

2. A process for the production of a cyclic amidine expressed by the following general formula (I):

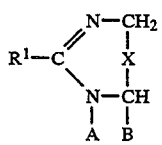

wherein $R^1$ stands for an aliphatic group, an alicyclic group, an aromatic group or a heterocyclic group, X stands for a direct bond or a divalent organic radical and A and B stand, independently from each other, for hydrogen or an organic group, comprising a step of reacting a nitrile having the following general formula (II):

$$R^1CN \qquad (II)$$

wherein $R^1$ has the same meaning as above, with a polyamine having the following general formula (III):

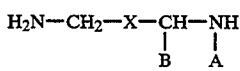

wherein X, A and B have the same meaning as above, at a temperature of 130°–250° C. in the presence of a mixture of water with a catalytically effective amount of a titanium compound.

3. A process as claimed in claim 2, wherein said titanium compound is an organic titanium compound, a titanium halide or titanium hydroxide.

4. A process as claimed in claim 3, wherein said organic titanium compound is a compound having the formula:

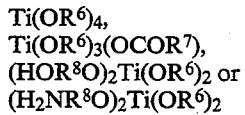

wherein $R^6$ and $R^7$ stand, independently from each other, for a hydrocarbyl group having 1–20 carbons and $R^8$ stands for an aliphatic or aromatic divalent radical having 1–20 carbons.

5. A process as claimed in claim 2, wherein said titanium compound is at least one member selected from the group consisting of titanium tetraisopropoxide, titanium tetra-n-butoxide, titanium tetrakis-2-ethyleneoxide, titanium tetrastearoxide, di-isopropoxybis(acetylacetonate)titanium, isopropoxy(2-ethyl-1,3-hexanedioleato)titanium, di-n-butoxybis(triethanolaminato)titanium, dihydroxybis(lactato)titanium, titanium tetrachloride, titanium tetrabromide, titanium tetrafluoride, titanium tetraiodide and titanium tetrahydroxide.

6. A process as claimed in claim 2, wherein said polyamine is expressed by the following formula (IV) or (V):

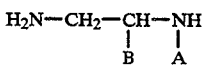

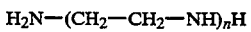

wherein A and B have the same meaning as above and n is an integer of 2-5.

7. A process as claimed in claim 6, wherein said polyamine is a member selected from the group consisting of 1,2-diaminoethane, 1,2-diaminopropane, 1,2-diamino-n-butane, 1,2-diamino-n-pentane, 1,2-diamino-n-hexane, 1,2-diamino-n-heptane, 1,2-diamino-n-octane, 1,2-diamino-n-nonane, N-benzylethylene-diamine, N-phenylethyelenediamine, N-methylethyelenediamine, N-ethylethylenediamine, 2-(2-aminoethylamino)ethanol, N-($\beta$-aminoethyl)-$\gamma$-aminopropyl(dimethoxy)-methylsilane, N-($\beta$-aminoethyl)-$\gamma$-aminopropyltrimethoxysilane, diethylenetriamine, triethylenetetramine, tetraethylenepentamine and pentaethylenehexamine.

8. A process as claimed in claim 2, wherein X is a divalent radical selected from the group consisting of alkylene, cycloalkylene, arylene, an aromatic radical having the formula —$R^2$—Ar—$R^2$— where $R^2$ and $R^3$ stand independently from each other for alkylene and Ar stands for arylene, and a radical having the formula

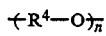

where $R^4$ stands for an alkylene and n is an integer of 1-5.

9. A process as claimed in claim 2, wherein said polyamine is a compound expressed by the formula (VI):

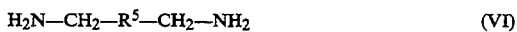

wherein $R^5$ is an alkylene having 1-22 carbon atoms.

10. A process as claimed in claim 9, wherein said polyamine is a member selected from the group consisting of 1,3-diaminopropane, 1,4-diaminobutane, 1,5-diaminopentane, 2,2-dimethylpropylenediamine, 1,6-diaminohexane, 1,7-diaminopentane, 1,8-diaminooctane, 1,9-diaminononane and 1,12-diaminododecane.

11. A process as claimed in claim 2, wherein said nitrile is a member selected from the group consisting of acetonitrile, propionitrile, benzonitrile, 1,3-dicyanobenzene, 1,4-dicyanobenzene, adiponitrile, lauronitrile, myristonitrile, palmitonitrile, stearonitrile, oleonitrile, caprylonitrile, caprylonitrile, arachidonitrile, behenonitrile and homopolymers and copolymers of acrylonitrile.

12. A process as claimed in claim 2, wherein said titanium compound is present in an amount of 0.1-5% based on the weight of said nitrile and said water is present in an amount of 1-300% by weight based on the weight of said titanium compound.

13. A process as claimed in claim 2, wherein said reacting step comprises the sub-steps of:
  reacting said titanium compound with said water to obtain a first mixture containing an oligomer of said titanium compound;
  removing unreacted water from said first mixture to obtain a second mixture containing said oligomer; and
  then reacting said nitrile with said polyamine in the presence of said second mixture.

14. A process as claimed in claim 2, wherein said reacting step comprises the sub-steps of:
  reacting said titanium compound with said water to obtain a first mixture containing an oligomer of said titanium compound; and
  then reacting said nitrile with said polyamine in the presence of said first mixture.

* * * * *